United States Patent
Yasutake et al.

(10) Patent No.: US 7,442,925 B2
(45) Date of Patent: Oct. 28, 2008

(54) WORKING METHOD USING SCANNING PROBE

(75) Inventors: Masatoshi Yasutake, Chiba (JP);
Takuya Nakaue, Chiba (JP); Kazutoshi Watanabe, Chiba (JP); Osamu Takaoka, Chiba (JP); Atsushi Uemoto, Chiba (JP); Naoya Watanabe, Chiba (JP); Yoshiteru Shikakura, Chiba (JP)

(73) Assignee: SII Nanotechnology Inc. (JP)

( * ) Notice: Subject to any disclaimer, the term of this patent is extended or adjusted under 35 U.S.C. 154(b) by 412 days.

(21) Appl. No.: 11/370,006

(22) Filed: Mar. 4, 2006

(65) Prior Publication Data
US 2006/0219901 A1    Oct. 5, 2006

(30) Foreign Application Priority Data

Mar. 8, 2005  (JP) ............................ 2005-063693
Jan. 27, 2006 (JP) ............................ 2006-018919

(51) Int. Cl.
*G01N 13/16*    (2006.01)

(52) U.S. Cl. ................ 250/307; 250/306; 250/310; 73/105

(58) Field of Classification Search ............... 250/307, 250/306, 310; 73/105
See application file for complete search history.

(56) References Cited

U.S. PATENT DOCUMENTS

2005/0092907 A1*  5/2005  West et al. ............... 250/234
2008/0048115 A1*  2/2008  Iyoki et al. ............... 250/306

* cited by examiner

*Primary Examiner*—Nikita Wells
(74) *Attorney, Agent, or Firm*—Adams & Wilks (57) ABSTRACT

The present invention provides a working method using a scanning probe which can enhance a working speed and prolong a lifetime of the probe. The present invention provides the working method using a scanning probe which works a sample by performing the relative scanning of a probe supported on a cantilever on the sample at a predetermined scanning speed. The working method can work the object to be worked while forcibly and relatively vibrating the probe in the direction orthogonal to or parallel to a working surface of the sample at low frequency of 100 to 1000 Hz.

20 Claims, 8 Drawing Sheets

WORKING METHOD USING SCANNING PROBE

BACKGROUND OF THE INVENTION

1. Field of the Invention

The present invention relates to a working method using a scanning probe in which a sample is worked using a scanning probe microscope (SPM) which acquires information on a measurement sample by performing the relative scanning of the measurement sample using a probe.

2. Description of the Related Art

As has been well-known, as an apparatus which measures a sample such as an electron material or the like in a minute region and performs the observation of a surface shape of the sample and the measurement of physical property information of the sample and the like, a scanning probe microscope (SPM) is used.

With respect to the scanning probe microscope, various type of scanning probe microscopes have been proposed. Among these scanning probe microscopes, there exists an atomic force microscope (AFM) referred to as a contact mode which brings a probe mounted on a distal end of a cantilever into contact with a surface of a sample with a fine force and manipulates the probe while controlling a distance between the probe and the sample such that a deflection quantity of the cantilever becomes a fixed value. Further, by making use of the property of the atomic force microscope, that is, the property that the probe is kept being in contact with the surface of the sample with the fine strength, there has been proposed a technique which applies desired fine working to the surface of the sample (see patent document 1, for example).

Further, there has been also proposed a technique in which ultrasonic vibrations in the vertical direction or in the horizontal direction are applied to a probe which is mounted on a distal end of a cantilever thus applying the more efficient fine working (see non-patent document 1, for example).

[patent document 1] Japanese Patent Laid-open 10(1998)-340700

[non-patent document 1] Futoshi Iwata, Akira Sasaki, "Ultrasonic TECHNO", Nihon Kogyo Schuppan, May 2002, 14 volume, No. 3, page 23-27)

SUMMARY OF THE INVENTION

However, the above-mentioned conventional working methods using the scanning probe microscope have following drawbacks. That is, the former working method is a method in which the working is performed by bringing the probe mounted on the distal end of the cantilever into contact with the surface of the sample with the fine force and hence, it is impossible to obtain a strong cutting force whereby the working efficiency is low. Due to this low working efficiency, there exist drawbacks that the working speed is low or a friction is generated due to the continuous contact between the probe and the working surface and the friction shortens a lifetime of the probe.

Further, in the latter working method, a cutting surface on a surface of the sample and the probe move at a high speed relative to each other. Accordingly, along with the enhancement of the working efficiency, particularly along with the enhancement of the working efficiency when the sample is made of a material having viscoelasticity such as plastic, some improvement is observed from a viewpoint of working speed. However, the working efficiency is still less than optimal and there has been a demand for further improvement of the working efficiency.

Further, to consider a case in which an optical mask having the two-layered film structure (MoSi/Glass) which forms molybdenum silicon on glass or the two-layered film structure (Cr/Glass) which forms chromium on glass is worked, since the upper MoSi film or Cr film is harder than the glass which constitutes a substrate, unless the upper film is not uniformly worked, the soft lower glass is cut through the worked portion of the upper film thus arising a drawback that the irregularities of the surface is increased.

The present invention has been made in view of the above-mentioned drawbacks and it is an object of the present invention to provide a working method using a scanning probe which can achieve the further enhancement of a working speed and the prolonged lifetime of the probe as well as the enhancement of flatness of the surface of an optical mask or the like having the two-layered film structure and reproducibility of working.

The present invention has, to overcome the above-mentioned drawbacks, adopted following constitutions. That is, according to the present invention, in a working method using a scanning probe which works an object to be worked by performing relative scanning of a probe which is supported on a cantilever at a predetermined scanning speed, the improvement is characterized in that the probe works the object to be worked in a state that the probe is forcibly vibrated in the direction orthogonal to a working surface of the object to be worked at low frequency of 100 to 1000 Hz.

Further, in a state that the probe is fixed at a predetermined working height from a reference surface of the object to be worked, the object to be worked is worked by scanning the probe in the X direction or in the Y direction parallel to a working surface of the object to be worked.

In the working method using the scanning probe according to the present invention, the probe is vibrated with a relatively small frequency of approximately 100 to 1000 Hz and hence, the probe impinges on a surface of the object to be worked in a form of a large mass system in which the probe is integrally formed with the probe supporting portion such as the cantilever. In this manner, different from the case in which only the probe impinges on the surface of the object to be worked, the probe 6a impinges on the surface of the object to be worked in the form of a certain degree of mass system including the cantilever 6 and hence, it is possible to impart a large impact force to a surface of the object to be worked. Accordingly, a cut quantity per one operation when the probe comes into contact with the surface of the sample is increased and, along with the enhancement of the working efficiency, the working speed is enhanced. Further, the contact between the distal end of the probe and the working surface is intermittent and hence, compared to a case in which the working is performed in a state that the probe is always held in contact with the working surface, it is possible to prolong the lifetime of the probe.

According to this invention, in a working method using a scanning probe which works an object to be worked by performing relative scanning of a probe which is supported on a cantilever on the object to be worked at a predetermined speed, the improvement is characterized in that the probe works the object to be worked in a state that the probe is forcibly vibrated in the direction parallel to a working surface of the object to be worked at low frequency of 100 to 1000 Hz.

In the working method using the scanning probe according to the present invention, the probe is forcibly vibrated in the direction parallel to the working surface of the object to be worked at the relatively low frequency of approximately 100 to 1000 Hz. Also in this case, it is possible to impart the large impact force to the surface of the object to be worked in the same manner as the above-mentioned invention and hence, along with the enhancement of the working efficiency, it is possible to achieve the enhancement of the working speed and the prolonged lifetime.

In the working method using a scanning probe according to the present invention, it is preferable that the probe works the object to be worked in a state that the probe is forcibly vibrated not only in the direction orthogonal to a working surface of the object to be worked but also in the direction parallel to the working surface of the object to be worked at low frequency.

According to this invention, it is possible to impart the impact force to the object to be worked in a resultant direction of the direction orthogonal to the working surface and the direction parallel to the working surface. This invention is particularly advantageous when, due to a shape of the object to be worked or the like, it is difficult to obtain the favorable working only with the forced vibrations at low frequency from the direction orthogonal to the working surface or only with the forced vibrations at low frequency from the direction parallel to the working surface.

In the working method using a scanning probe according to the present invention, it is preferable that the object to be worked is worked by setting an amplitude when the probe is forcibly vibrated at low frequency to a value which falls within a range of 5 to 2000 nm.

According to this invention, by applying the vibrations with the relatively large amplitude, it is possible to further enhance the working efficiency thus further enhancing the working speed and, at the same time, further prolonging the lifetime.

In the working method using a scanning probe according to the present invention, it is preferable that the object to be worked is worked in a state that the probe is forcibly vibrated at low frequency and, at the same time, the object to be worked is relatively resonated at frequency higher than the low frequency in the direction orthogonal to a working surface of the object to be worked.

According to this invention, the object to be worked is worked in a state that the probe is forcibly vibrated at the relatively low frequency and, at the same time, the object to be worked is relatively resonated with the high frequency in the direction orthogonal to the working surface of the object to be worked and hence, the working surface of the object to be worked and the probe move at a high speed relative to each other whereby, it is possible to enhance the working efficiency, particularly, when the object to be worked possesses viscoelasticity as in the case of plastic or the like.

In the working method using a scanning probe according to the present invention, it is preferable that the object to be worked is worked in a state that the probe is forcibly vibrated at low frequency and, at the same time, the object to be worked is relatively resonated at frequency higher than the low frequency in the direction parallel to a working surface of the object to be worked.

According to this invention, the object to be worked is worked in a state that the probe is forcibly vibrated at relatively low frequency and, at the same time, the object to be worked is relatively resonated with the high frequency in the direction parallel to a working surface of the object to be worked and hence, the working surface of the object to be worked and the probe move at a high speed relative to each other in the same manner as the above-mentioned invention whereby, it is possible to enhance the working efficiency, particularly, when the object to be worked possesses viscoelasticity as in the case of plastic or the like.

In the working method using a scanning probe according to the present invention, the vibrations are applied to the probe while setting the vibration frequency to the relatively low frequency of approximately 100 to 1000 Hz and hence, the probe impinges on the surface of the object to be worked in a form of a relatively large mass system in which the probe is integrally formed with the probe supporting portion such as the cantilever. Accordingly, the cut quantity per one operation when the probe comes into contact with the surface of the sample is increased and, along with the enhancement of the working efficiency, the working speed is enhanced.

Further, the lifetime of the probe can be enhanced.

Still further, along with the enhancement of the working efficiency, it is possible to ensure the same working quantity with the small number of workings and hence, the working irregularities can be reduced whereby the leveling of the working can be easily ensured and, at the same time, the controllability of the working can be also enhanced.

Still further, even when an optical mask having the two-layered film structure or the like is to be worked, there is no possibility that an upper hard film is excessively worked and hence, a surface of the optical mask can be worked into a flat surface.

BRIEF DESCRIPTION OF THE DRAWINGS

FIG. 2A and FIG. 2B are views showing an example of a case in which cutting working is performed in accordance with the method of the present invention, wherein

FIG. 6A and FIG. 6B are views showing a comparison when the cutting working is performed by the method of the present invention and when the cutting working is performed by a conventional method, wherein

FIG. 7A and FIG. 7B are views showing the relationship between the number of scanning and a working depth when the cutting working is performed by the method of the present invention and when the cutting working is performed by a conventional method, wherein FIG. 7A shows the relationship between the number of scanning and the working depth when the cutting working is performed by the conventional method and FIG. 7B shows the relationship between the number of scanning and the working depth when the cutting working is performed by the method of the present invention;

DESCRIPTION OF THE PREFERRED EMBODIMENTS

Embodiments of a working method using a scanning probe according to the present invention are explained in conjunction with drawings.

Before explaining the method of the present invention, a scanning probe microscope which is capable of preferably carrying out the method of the present invention is explained.

Figure 1:
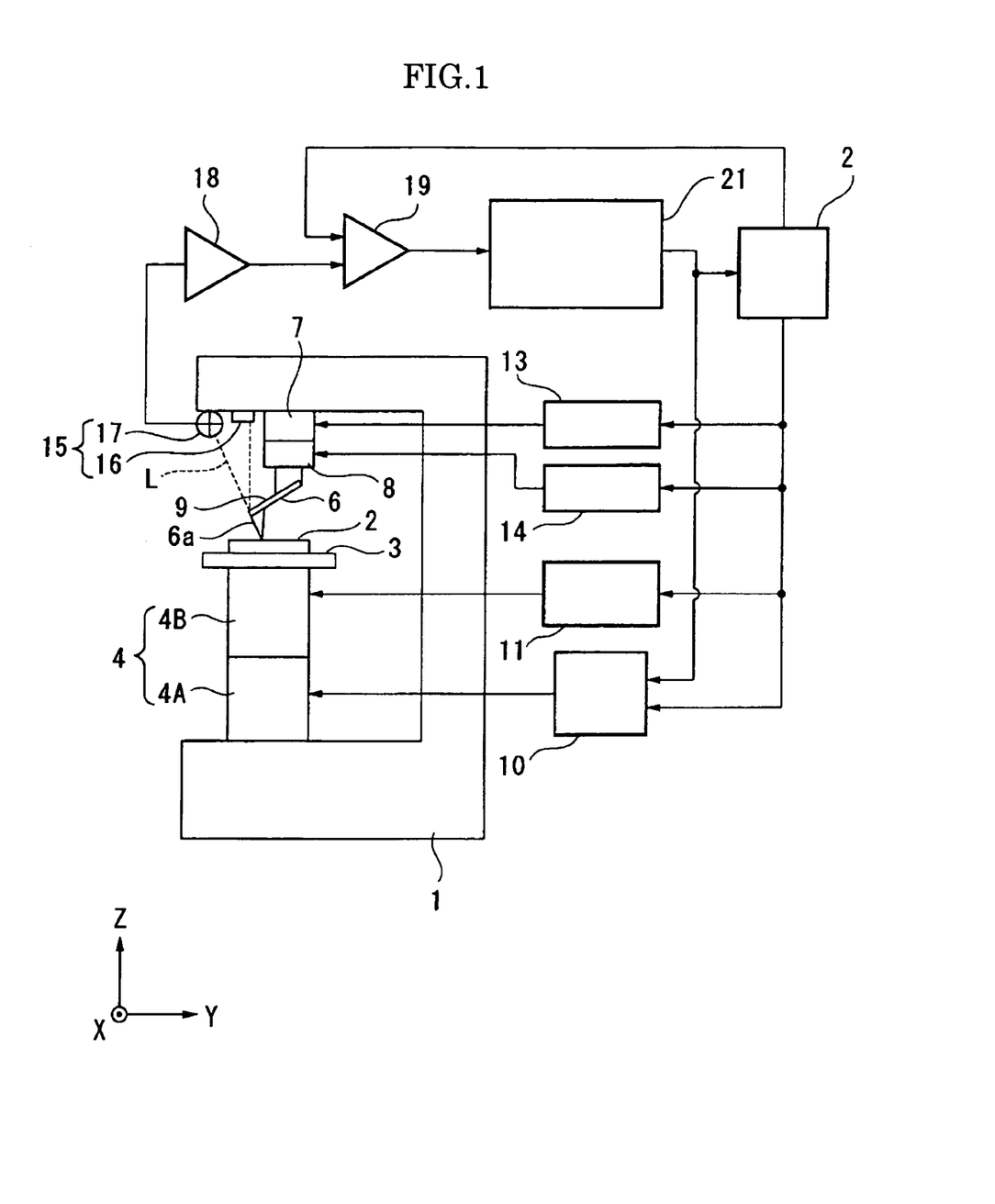
FIG. 1 is a block diagram showing a scanning probe microscope used in carrying out a method of the present invention.

In the drawing, numeral 1 indicates a base frame. On a predetermined portion of a lower portion of the base frame 1, a sample base 3 which mounts a sample 2 which constitutes an object to be worked thereon is mounted in a state that the sample base 3 is movable in the XY directions as well as in the Z direction by way of a scanner 4. The scanner 4 is, for example, constituted of a Z scanner 4A which moves the sample base 3 in the Z direction (vertical direction) and a XY scanner 4B which moves the sample base 3 in the XY directions (horizontal directions). On a predetermined portion of an upper portion of the base frame 1, a probe 6 is supported in a state that the probe 6 faces the sample 2, wherein the probe 6 can be resonated in the X direction or in the Y direction by way of an XY resonance piezoelectric plate 7 and, further, the probe 6 can be resonated in the Z direction by way of a Z resonance piezoelectric plate 8.

The probe 6 is configured such that a probe 6a is mounted on a distal end of a cantilever 9, and a deflection change of the cantilever 9 is detected by a detecting means 15.

The above-mentioned Z scanner 4A is controlled such that a voltage is applied to the Z scanner 4A by a Z scanner controlling power source 10 so that a pushing force of the probe 6a to the sample 2 assumes a fixed value in average and, at the same time, the Z scanner 4A is controlled such that the probe 6a is forcibly vibrated in the direction orthogonal to a working surface of the sample 2 with relatively low frequency relative to the sample 2. Further, the XY scanner 4B is controlled such that a voltage is applied to the XY scanner 4B by a XY scanner controlling power source 11 so that the probe 6a can perform preliminarily fixed scanning with respect to the sample 2 and, at the same time, XY scanner 4B is controlled such that the vibrations are forcibly applied to the probe 6a in the direction (for example, the X direction or the Y direction) parallel to the direction a working surface of the sample 2 with relatively low frequency. The relatively low frequency is, with respect to both of the Z scanner 4A and the XY scanner 4B, approximately 100 to 1000 Hz. Further, an amplitude of the vibrations is, with respect to both of the Z scanner 4A and the XY scanner 4B, approximately 5 to 2000 nm.

The driving of the XY resonance piezoelectric plate 7 is controlled by an XY resonance piezoelectric plate controlling power source 13, while the driving of the Z resonance piezoelectric plate 8 is controlled by a Z resonance piezoelectric plate controlling power source 14. The vibration frequency of the probe 2a which is resonated by the XY resonance piezoelectric plate controlling power source 13 and the Z resonance piezoelectric plate controlling power source 14 by way of the XY resonance piezoelectric plate 7 and the Z resonance piezoelectric plate 8 is set higher than the frequency vibrated by the Z scanner 4A or the XY scanner 4B, that is, approximately 100 kHz to 5 MKz, for example. Further, the vibration amplitude of the probe 2a which is resonated by way of the XY resonance piezoelectric plate 7 and the Z resonance piezoelectric plate 8 is set to a value smaller than the vibration amplitude by the Z scanner 4A and the XY scanner 4B, for example, 0.5 to 500 nm.

The detecting means 15 includes a laser generator 16 which irradiates a back surface of the cantilever 9 with laser beams L and a cantilever displacement detector 17 which receives a laser light L which is reflected on the back surface of the cantilever 9. The cantilever displacement detector 17 is constituted of a four-split light detecting electrode, for example, wherein the cantilever displacement detector 17 is positioned such that a spot of the laser beams L reaches the center of the four-split light detecting electrode when a strain quantity of the cantilever 6 is 0. Further, the cantilever displacement detector 17 is electrically connected with a displacement amplifying pre-amplifier 18, while the displacement amplifying pre-amplifier 18 is electrically connected with an error detector 19. In the error detector 19, a set value which is set by a control part body 20 and an output value from the displacement amplifying pre-amplifier 18 are compared to each other, and the difference is outputted a Z servo system control part 21 in a form of an electric signal. A control signal is supplied to the Z scanner control electric source 10 from the Z servo system control part 21, and a distance between the probe 6a and the sample 2 is controlled such that a deflecting quantity of the cantilever 9 becomes fixed in response to the control signal.

Further, the control signals are transmitted to the Z scanner controlling power source 10, the XY scanner controlling power source 11, the Z resonance piezoelectric plate controlling power source 14, and the XY resonance piezoelectric plate controlling power source 13 from the control part body 20 so as to apply the forced vibrations in the Z direction, X direction and the Y direction at low frequency and the resonance vibrations in the Z direction, X direction and the Y direction at high frequency to the probe 6a.

Figure 2:
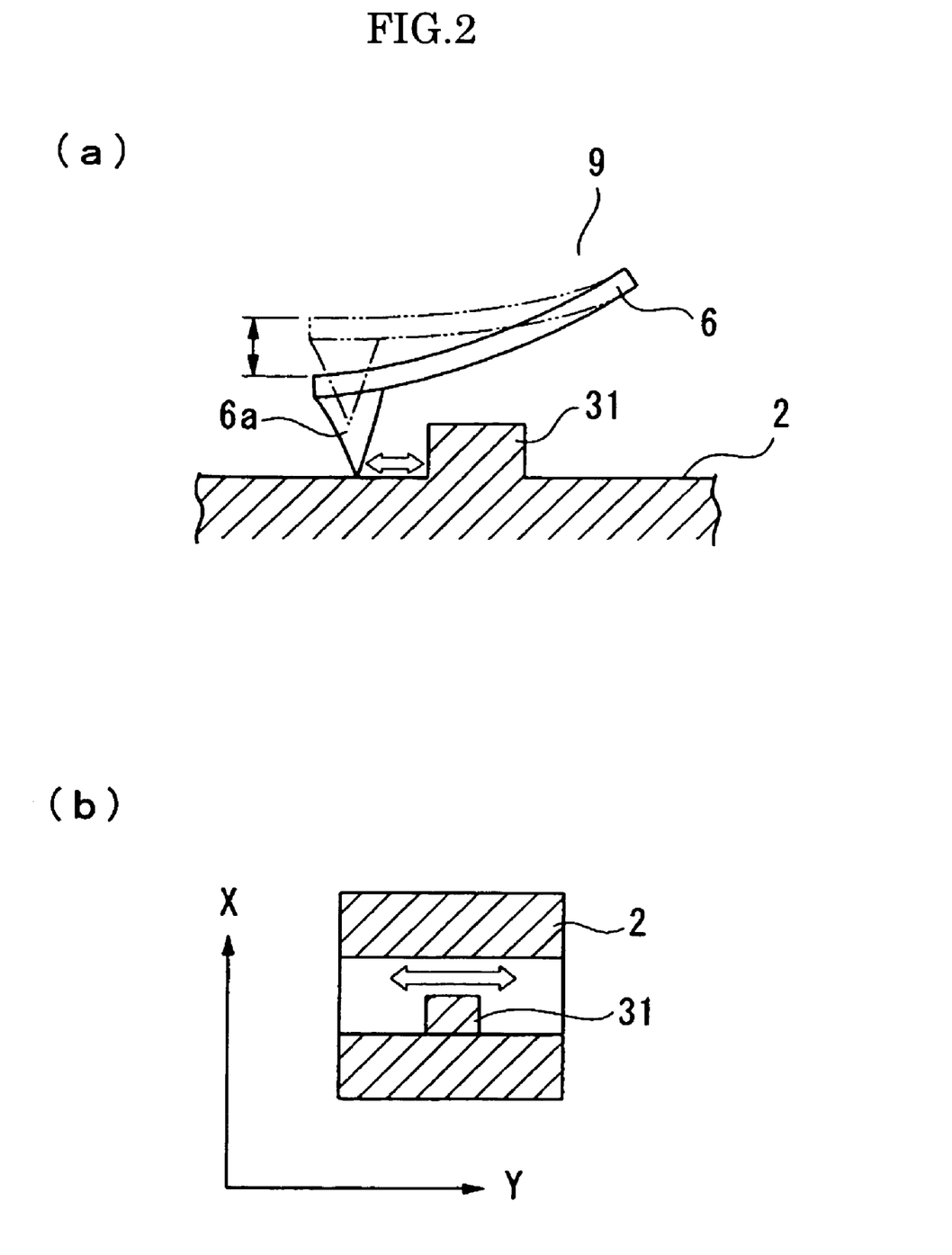
FIG. 2A is a cross-sectional view and FIG. 2B is a plan view.

Next, the working method which performs the cutting working of the sample using the scanning probe microscope having such a constitution is explained. FIG. 2 shows an example in which a defect 31 of an optical mask which constitutes the sample 2 is corrected by the working method of the present invention.

First of all, to the control part body 20 shown in FIG. 1, by way of a setting part not shown in the drawing, the low frequency when the probe 6a is vibrated forcibly and relatively in the direction orthogonal to the working surface of the sample 2 (in the Z direction in FIG. 1), an area to be worked, and a scanning speed at which the sample base 3 is scanned in the XY scanning direction are respectively inputted.

Then, when a start button not shown in the drawing is pushed, the sample base 3 is forcibly vibrated in the Z direction at a set predetermined low frequency by the Z scanner 4A. Further, at the same time, based on a signal which is generated from the control part body 20, the Z scanner 4A is operated by way of the Z scanner controlling power source 10 and hence, the sample base 3 is moved in the Z direction so as to allow the surface of the sample 2 to approach the probe 6a.

Then, when the sample 2 approaches the probe 6a with a fixed distance therebetween, the detecting means 15 detects a deflection quantity of the cantilever 9 thereafter. Then, based on a detection result, the distance between the probe and the sample is controlled such that the deflection quantity becomes a fixed value.

Figure 3:
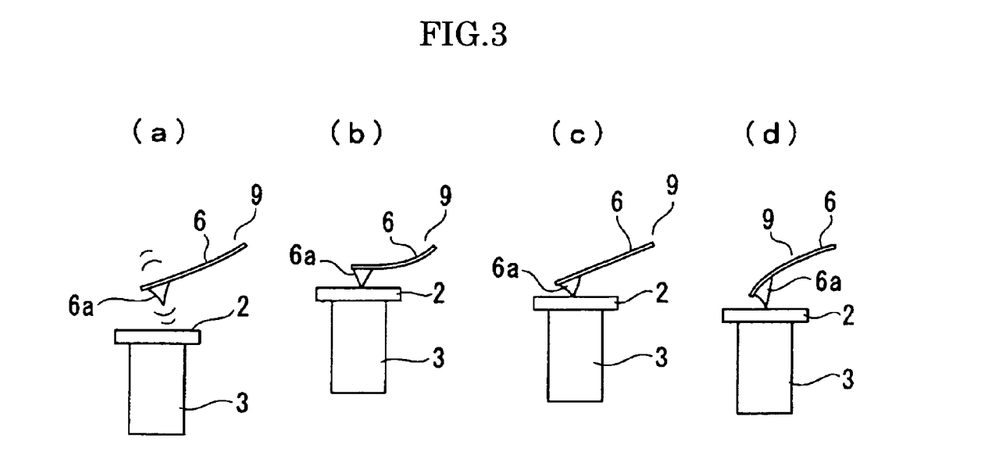
FIG. 3A to FIG. 3D are side views for explaining the behavior of a probe when the cutting working is performed by the method of the present invention.
Figure 4:
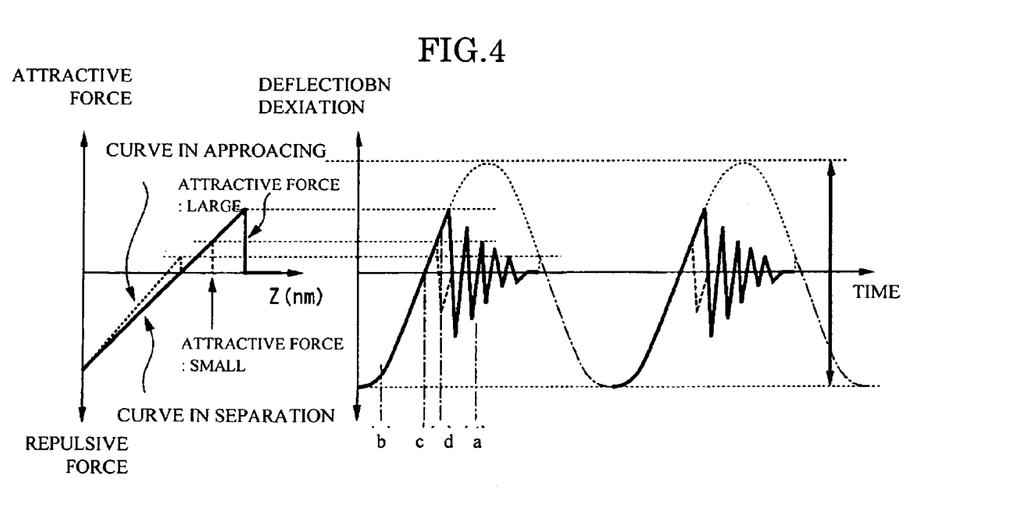
FIG. 4 is a view for explaining the behavior of a sample base and a probe when the cutting working is performed by the method of the present invention.

FIG. 3 and FIG. 4 show the relationship between the probe 6a and the semiconductor mask 2 which constitutes the sample. Due to an action of the Z resonance piezoelectric plate 8, the probe 6a is moved upwardly and downwardly while depicting a sinusoidal wave in the Z direction. The probe 6a is, although not being in contact with the sample 2 (FIG. 3A) first of all, brought into contact with the semiconductor mask 2 along with the elevation of the sample base 3 and, further, the cantilever 6 is deflected due to the elevation of the sample base 3 (FIG. 3B). Thereafter, although the sample base 3 is lowered, the probe 6a is kept into contact with the semiconductor mask 2 and, even after the sample base 3 reaches an origin position of the sinusoidal wave, the probe 6a is kept into contact with the semiconductor mask 2 due to the viscosity of the semiconductor mask 2 (FIG. 3C, FIG. 3D). Thereafter, when the sample base 3 is further lowered, the probe 6a is separated from the semiconductor mask 2. Since the cantilever 6 is in a deflected state when the cantilever 6 is separated, after separation, a distal end of the cantilever 6 and the probe 6a are vibrated in the Z direction and, thereafter, the vibrations are attenuated. Hereinafter, the sample is subject to the cutting working by the distal end of the probe 6a by repeating the behaviors shown in FIG. 3A to FIG. 3D. FIG. 3A to FIG. 3D correspond to (a) to (d) in FIG. 4 respectively.

Here, since the sample base 3 is vibrated by the scanner 4A at the relatively low frequency of approximately 100 to 1000 Hz, the probe 6a impinges on a surface of the semiconductor mask 2 in a form that the probe 6a is integrally formed with a probe supporting portion such as the cantilever 6 or the like or in a form of mass system. In this manner, different from the case in which only the probe 6a impinges on the surface of the semiconductor mask 2, the probe 6a impinges on the surface of the semiconductor mask 2 in the form of a certain degreed of mass system including the cantilever 6 and hence, it is possible to impart a large impact force to the surface of the semiconductor mask 2. Accordingly, a working quantity per one contact of the probe 6a with the surface of the semiconductor is increased and, along with the increase of the working efficiency, it is possible to achieve the enhancement of the working speed and the prolonged lifetime of the probe.

Here, the reason that vibration frequency of the sample base 3 is set to approximately 100 to 1000 Hz is as follows. When the vibration frequency of the sample base 3 is equal to or less than 100 Hz, the number of impingement between the semiconductor mask 2 which constitutes the sample and the probe 6a per hour is decreased and hence, the working speed is decreased. Further, when the vibration frequency of the sample base 3 is approximately 1000 Hz or more, the vibration frequency is excessively high and hence, a portion of the cantilever 6 which is close to a proximal end side than a middle portion of the cantilever 6 is hardly moved upwardly and downwardly, whereby only the distal end portion of the cantilever 6 is vibrated in the vertical direction together with the probe 6a. Accordingly, when the probe 6a impinges on the semiconductor mask 2, the probe 6a cannot perform the impingement with the large mass system whereby there arises a drawback that the working efficiency is lowered.

Further, the amplitude of the vibrations of the sample base 3 generated by the scanner 4A is set to 5 to 2000 nm. When the amplitude is set lower than 5 nm, the probe 6a cannot deeply cut the semiconductor mask 2 and hence, the working efficiency is lowered correspondingly. Further, when the amplitude is set larger than 2000 nm, the amplitude is simply increased and the working efficiency reaches an upper limit and hence, it is not possible to achieve the further enhancement of the working efficiency whereby the energy necessary for applying the vibrations is simply wasted.

Figure 5:
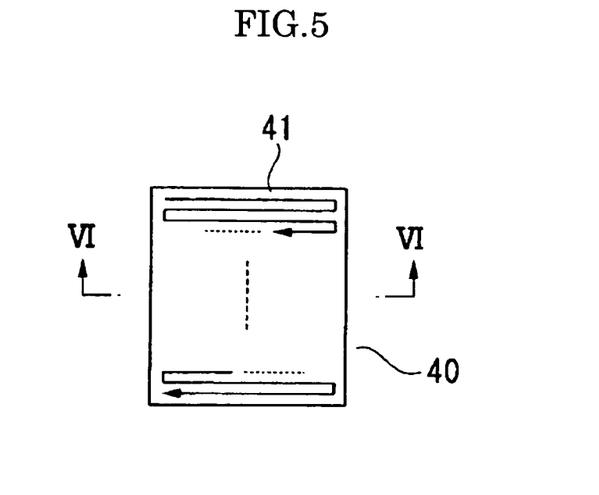
FIG. 5 is a plan view for explaining a sample which is subject to cutting working performed by the method of the present invention.

A comparison is made between the case of the method of the present invention in which the working is performed by forcibly vibrating the probe at the low frequency and the case of the conventional method in which the working is performed without applying the relative vibrations to the probe. To be more specific, as shown in FIG. 5, the comparison of the method of the present invention and the conventional method is made with respect to a case in which a square portion 41 having one side of 1 μm is worked by cutting in a test mark 40 of an optical mask. Hereinafter, a result of the comparison is described hereinafter.

Here, in cutting the square portion 41 of 1 μm, the number of cutting lines is set to 32 lines. A diamond needle is used as a probe.

Figure 6:
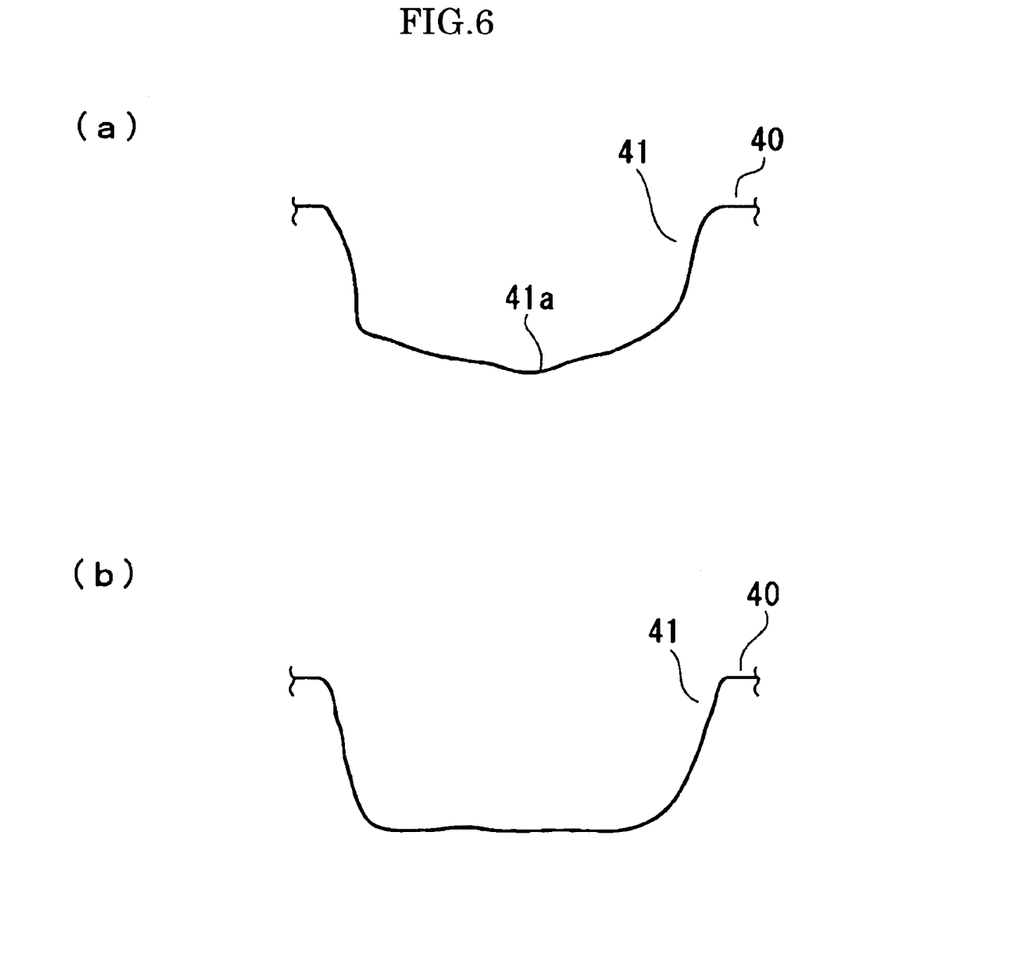
FIG. 6A is a cross-sectional view when the cutting working is performed by the conventional method and FIG. 6B is a cross-sectional view when the cutting working is performed by the method of the present invention.

FIG. 6A and FIG. 6B are cross-sectional views of the test mark 40 after working taken along a line VI-VI in FIG. 5. As can be clearly understood from the drawing, in a conventional working method shown in FIG. 6A, a bottom-surface center portion 41a is deeply dug and is formed into an approximately bowl shape as the whole bottom surface of the square portion 41, while in the working method of the present invention shown in FIG. 6B, the working is performed such that a bottom surface of the square portion 41 is uniformly leveled. This implies that, according to the present invention, by fixing the working conditions, it is possible to perform the uniform cutting working.

Further, although not shown n the drawing, the comparison of the working depth is performed. While the working depth is 16 nm in the conventional working method, the working depth is 20 nm in the working method of the present invention. Here, as the working conditions, a probe weight is set to 177 μN, a prove speed is set to 2000 nm/sec, a scanning time is set to two times, and a working time is 64 sec.

Figure 7:
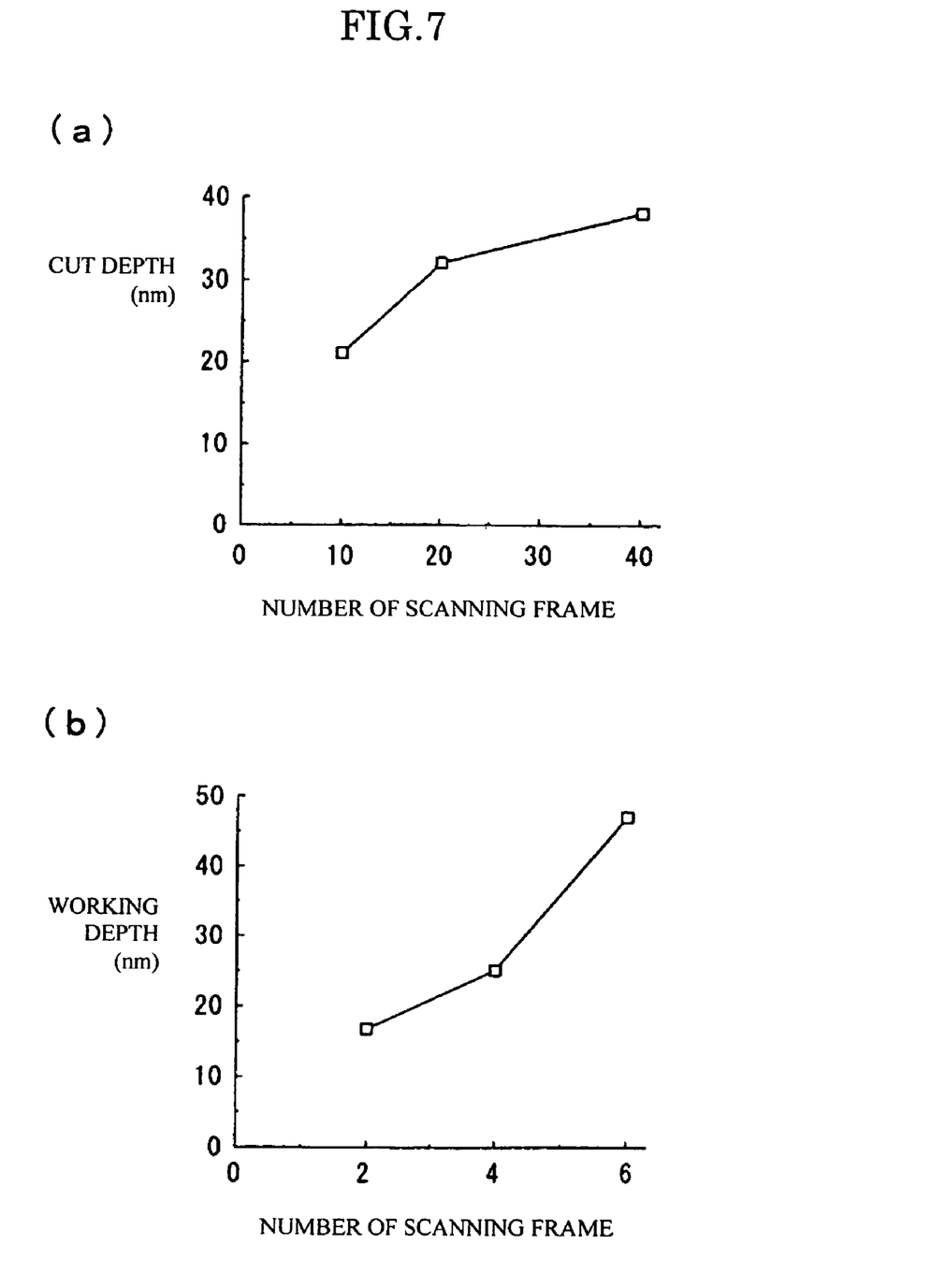

Further, FIG. 7A and FIG. 7B show the correlation between the number of scanning and the cutting depth between the case of the method of the present invention and the case of the conventional method. In FIG. 7A and FIG. 7B respectively, the number of scanning (times) is taken on an axis of abscissas and the cut depth (nm) is taken on an axis of ordinates. As can be understood from these drawings, in cutting the test mark 40 with a depth of 30 nm, according to the conventional method, as shown in FIG. 7A, it is necessary to perform the scanning approximately 20 times, while according to the method of the present invention, it is possible to complete the working by performing the scanning 4 to 5 times. This is, as mentioned above, a result which can be predicted based on the difference in cutting depth per one scanning, as a matter of course. Further, it is understood that based on the comparison of the cases shown in FIG. 7A and FIG. 7B, although the working speed is lowered when the cutting depth is large in the conventional method, the cutting speed is not lowered but is increased contrary when the cutting depth becomes large according to the method of the present invention.

Here, under such working conditions, while the deflection of the cantilever is 50 nm in the conventional method, the deflection of the cantilever is 20 nm in the present invention. It is understood from this fact that the method of the present invention allows the cutting with the weaker force than the conventional method.

Figure 8:
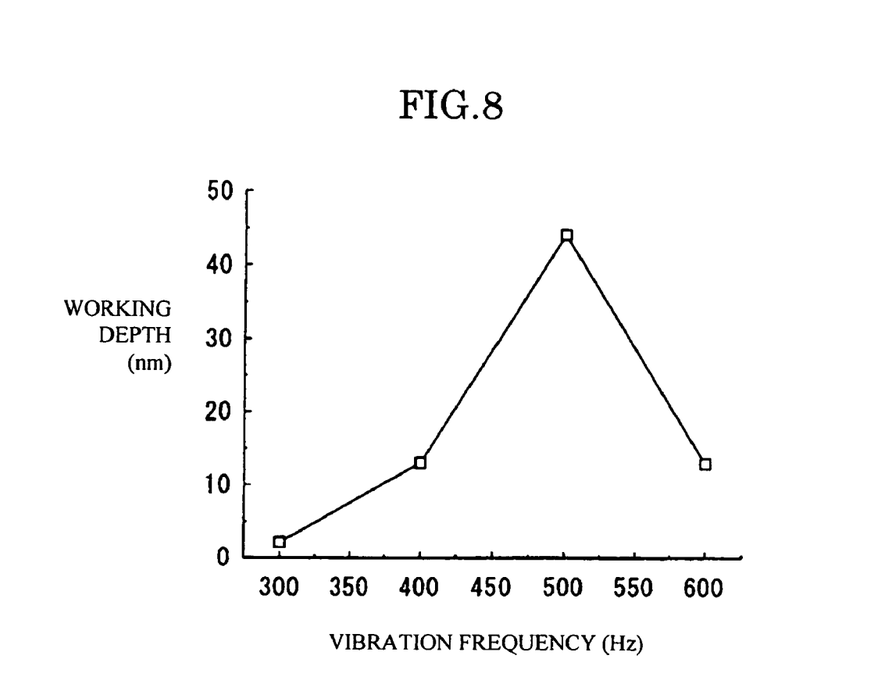
FIG. 8 is a view showing the relationship between the vibration frequency and the working depth when the cutting working is performed by the method of the present invention.

FIG. 8 shows the relationship between the frequency and the working depth when the sample base 3 is vibrated at low frequency when the cutting working is performed in the method of the present invention. As can be understood from the drawing, along with the increase of the vibration frequency from 300 Hx to 400 Hz and, thereafter, from 400 Hz to 500 Hz, while when the vibration frequency exceeds 500 Hz, the working depth is decreased to the contrary. That is, it is understood that the vibration with the frequency of approximately 500 Hz is most efficient in the cutting working.

Figure 9:
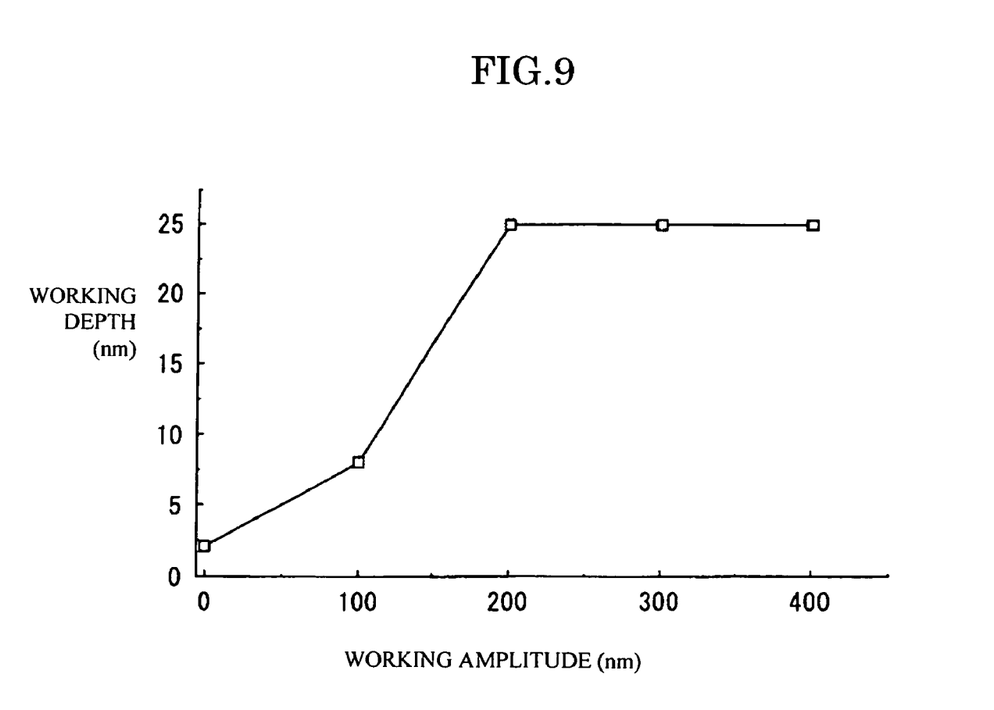
FIG. 9 is a view showing the relationship between the vibration amplitude and the working depth when the cutting working is performed by the method of the present invention.

FIG. 9 shows the relationship between the vibration amplitude and the working depth when the sample base 3 is vibrated at low frequency when the cutting working is performed in the method of the present invention. As can be understood from the drawing, when the vibration amplitude is gradually increased from 0, the working depth is also increased correspondingly, and when the vibration amplitude exceeds 100 nm, the working depth is further increased. To the contrary, when the working depth exceeds 200 nm, the working depth is held at a fixed value and is no more increased. From this fact, it is understood that even when the vibration amplitude is increased, the working depth reaches an upper limit at a certain value.

Here, the vibration amplitude with which the working depth arrives at the upper limit differs depending on the working conditions.

In the above-explained embodiment, the sample base 3 is forcibly and relatively vibrated at low frequency. However, in place of such vibrations, the probe 6a side may be vibrated at low frequency. Due to such vibrations, the probe 6a is vibrated with respect to the sample 2.

Further, in the above-mentioned embodiment, the probe 6a is forcibly vibrated at low frequency only in the direction orthogonal to the working surface of the sample 2. However, in place of such vibrations, the probe 6a may be forcibly vibrated at low frequency in the direction parallel to the working surface of the sample 2. In this case, the probe 6a may be forcibly vibrated only in one direction out of two directions consisting of the X direction and the Y direction. Further, in this case, the probe 6a may be forcibly vibrated at low frequency in both of the direction orthogonal to the working surface of the sample 2 and the direction parallel to the working surface of the sample 2. It is confirmed that this can obtain the substantially equal advantageous effects as the methods explained in conjunction with the above-mentioned embodiments.

Further, when the probe 6a is vibrated at low frequency in one direction (Z direction, X direction or Y direction) or when the probe 6a is vibrated at low frequency in both directions (Z direction and X direction, or Z direction and Y direction), in addition to the vibrations at low frequency, the surface of the sample 2 may be worked by resonating the probe 6a in the X direction or the Y direction using the XY resonance piezoelectric plate 7 shown in FIG. 1, or by resonating the probe 6a in the Z direction using the Z resonance piezoelectric plate 8 shown in FIG. 1, or by resonating the probe 6a in the X direction or the Y direction using the XY resonance piezoelectric plate 7 and, at the same time, by resonating the probe 6a in the Z direction using the Z resonance piezoelectric plate 8.

In this case, the frequency used for resonating the probe 6a is frequency which is far higher than the frequency used for performing the vibrations by the Z scanner or the XY scanner, that is, approximately 100 KHz to 5 MHz, for example, wherein the resonance frequency is 0.5 to 500 nm.

Next, as the second embodiment, the explanation is made with respect to a working method which applies the cutting working to the sample using the scanning probe microscope having the above-mentioned constitution. FIG. 2 shows an example in which a defect 31 of the optical mask which constitutes the sample 2 of the object to be worked is corrected using the working method of the present invention.

Next, the case in which the two-layered film such as an optical film which is formed by stacking molybdenum silicon on glass (MoSi/Glass) or by stacking chromium on glass (Cr/Glass) is explained.

This working mode is a working mode in which a working probe is arranged at a predetermined height (slice height) of the object to be worked, the Z servo is fixed during the working so as to stop the movement of the Z scanner, and the object to be worked is cut with pressure in the lateral direction. Here, the method is referred to as a slice mode.

In this working method, different from the conventional contact mode, that is, the mode in which the distance between the probe 6a and the sample 2 is controlled to allow the deflection quantity of the cantilever 9 to assume a fixed value, the distal end of the probe cannot move to a height below a predetermined height and the object to be worked is worked at a fixed height (depth) from the reference surface.

The detail of the manner of operation of the probe in this mode is hereinafter explained by taking the cutting working of the optical mask having the two-layered film shown in FIG. 10 to FIG. 12 as an example.

Figure 10:
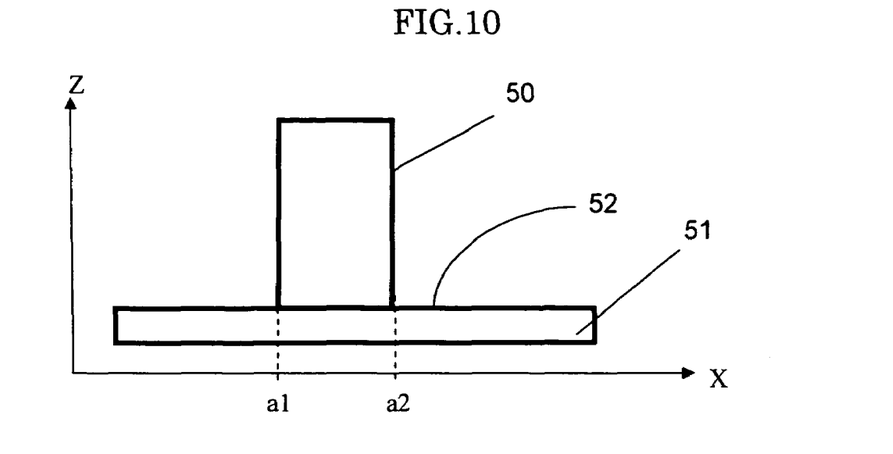
FIG. 10 is a cross-sectional view for explaining an optical mask formed of a two-layered film which is subjected to the cutting working of the second embodiment of the method of the present invention.

FIG. 10 is a cross-sectional view of the optical mask formed of the two-layered film which is worked by this mode and shows a pattern in which chromium (Cr) 50 which constitutes the object to be worked by cutting working is formed on glass 51 as an example.

Figure 11:
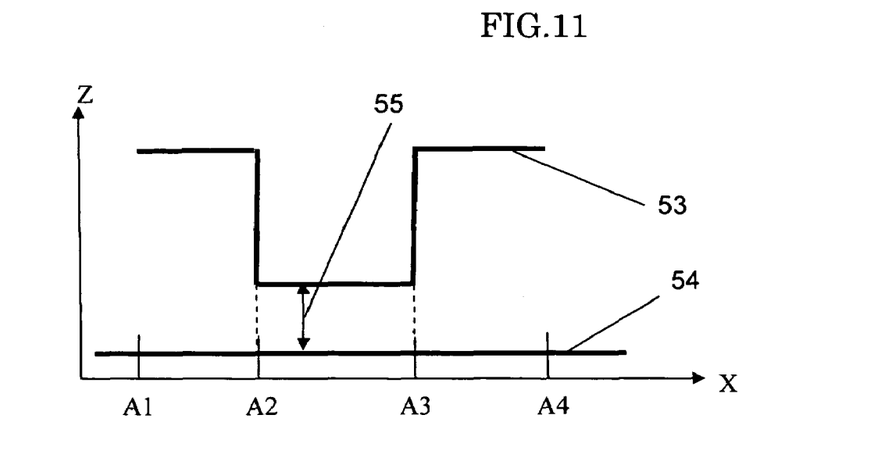
FIG. 11 is a side view for explaining the behavior of a probe when the cutting working of the second embodiment of the method of the present invention is performed.

FIG. 11 is a side view for explaining a trajectory of the Z-directional height of the probe of the cantilever 9 when the cantilever scanning is performed for working the optical mask.

Figure 12:
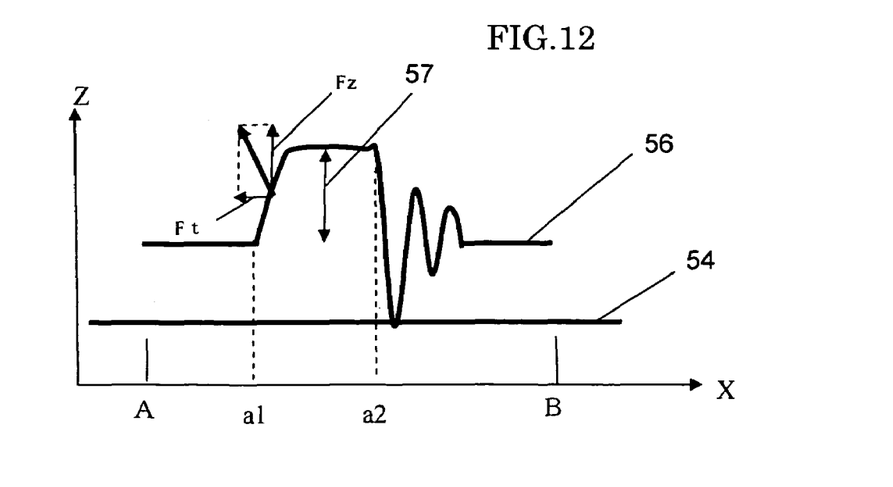
FIG. 12 is a side view for explaining of the behavior of a deflection quantity of a cantilever when the cutting working of the second embodiment of the method of the present invention is performed.

FIG. 12 is a side view for explaining the behavior of the deflection quantity of the cantilever 9 which is detected by the detecting means 15 when the cantilever 9 is scanned and the optical mask is worked.

First of all, by manipulating the probe such that the probe mounted on the distal end of the cantilever is vibrated in the direction orthogonal to the surface of the glass 51 and, at the same time, the distance between the probe and the sample is controlled to allow an amplitude attenuation ratio of the cantilever or the shift of the frequency assumes a fixed value, the measurement of the surface shape of the scanning region including the working region is performed.

Next, three arbitrary positions on the glass surface 52 are selected based on the measured data of the surface shape, and the inclination of the glass surface 52 is obtained, wherein when the inclination value is equal to or below a predetermined value, an average value of respective measured values is obtained, and the obtained value which becomes the reference height is set as a reference point 54.

Next, the setting of the scanning regions (A1 to A4) and the working height (55) shown in FIG. 10 to FIG. 12 and the setting of the working regions (a1 to a2) are performed. The working height 55 sets the distance between the probe which is mounted on the distal end of the cantilever and the above-mentioned reference point.

First of all, the scanning of the probe of the cantilever is started from A1 on the X axis outside the working region at a height sufficiently remote from the reference position 54.

Next, when the probe 6a is scanned to the working region (A2 on the X axis), the probe is allowed to approach by the Z scanner 4A until the probe assumes the working height (slice height) 55 and is fixed.

When the side surface of the probe 6a is brought into contact with the working surface of chromium (Cr) 50 which constitutes the object to be worked, a resultant force of a force Ft in the X direction and a force Fz in the Z direction which the probe 6a imparts to the working surface of the sample is imparted to the working surface so as to work chromium which constitutes the object to be worked.

Here, Fz is a value obtained by multiplying a Z-directional spring constant Kz of the cantilever with a deflection quantity 57 of the cantilever by the object to be worked with respect to a state 56 in which the cantilever has no deflection. Accordingly, in the state 56 that the cantilever has no deflection or when the height of the working surface is equal to or below the working height (slide height) 55, the force Fz in the Z direction is not imparted.

It is possible to monitor the Z-directional displacement of the cantilever as a deflection signal Bs=Fz/Kz of the cantilever.

Further, the force Ft in the X direction which is the horizontal direction with respect to the working surface is obtained by multiplying a twisting quantity of the distal end of the probe with the spring coefficient Kt in the twisting direction of the cantilever. The force Ft does not depend on the scanning speed, that is, the cutting speed.

Next, when the probe 6a is scanned up to the working region (A3 on the X axis), the probe is released from the object to be worked, wherein the probe 6a is vibrated with the maximum amplitude.

When the amplitude is larger than the working height (slice height) 55, there arises a possibility that the probe is brought into contact with the glass surface 52 and generates flaws on the glass. To prevent such a drawback, at a point of time that the probe passes chromium (Cr) 50 which constitutes the object to be worked, the probe 6a is separated from the working surface of chromium (Cr) 50 which constitutes the object to be worked and the scanning is performed.

As described above, the prevention of the flows after working is performed by pulling up the probe in the region outside the working region as mentioned previously.

Further, the working height (slice height) 55 is set such that the working height becomes larger than the amplitude due to the release of the probe (hereinafter referred to as opening amplitude), wherein the releasing magnitude is controlled to a relatively small value.

However, at the time of performing the final working, the working height 55 is set to 0 or less than 0. Accordingly, although the release vibrations are generated in the scanning of the final working, the release amplitude is a small value and hence, the vibrations which generate flaws can be made small.

For example, in case of continuously working an isolated defect (height h=70 nm), by setting the working height, that is, the height from the bottom surface to 46 nm, 30 nm, 20 nm, 13.2 nm, 8.7 nm, . . . (S1=2 h/3, Si+1=2/3×Si), the flaws are hardly generated.

The deflection signal of the cantilever is converted into a height signal during working and can be monitored.

The method for calibrating the deflection signal of the cantilever to the height signal is carried out such that a flat sample is allowed to approach in a contact mode and, thereafter, is pushed by a fixed quantity. The deflection signal which is proportional to the push-in quantity is generated. The push-in quantity is varied and a calibration curve between the push-in quantity and the deflection signal is obtained.

As described above, during a period in which the probe is scanned in the working region, the probe is allowed to approach the working height using the Z scanner 4A and is fixed at the working height. Accordingly, a working force is not applied unless the probe does not reach the predetermined working height and hence, an interface of the two-layered film made such as molybdenum silicon on glass (MoSi/Glass) or chromium (Cr/Glass) on glass such as the optical mask can be worked flatly.

Figure 13:
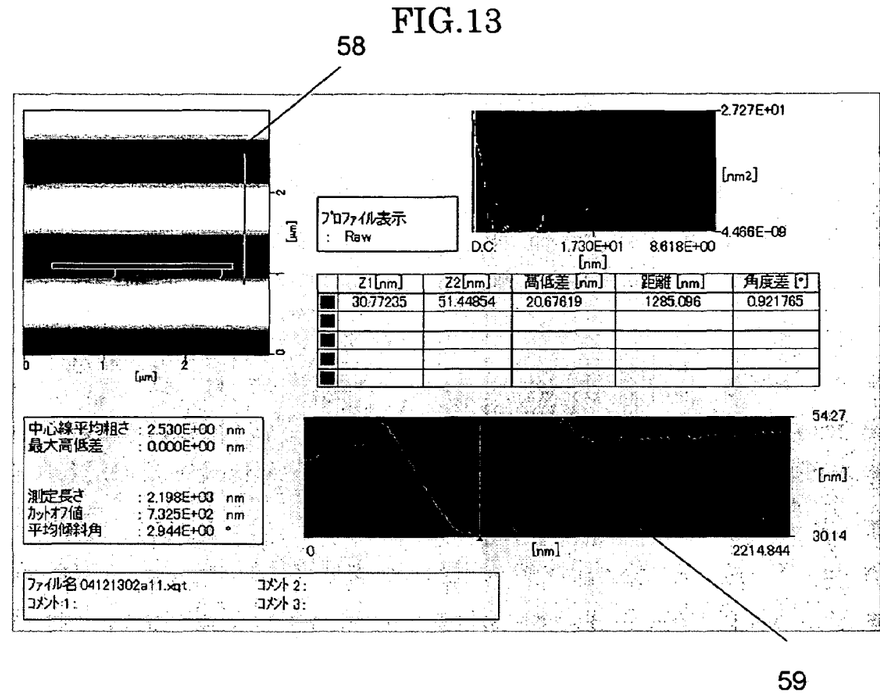
FIG. 13 is a view showing a measurement screen exemplifying an example of working in a contact mode.

FIG. 13 is a measurement screen showing a working example of a contact mode, wherein a post-working plan view 58 and an average cross-sectional view 59 of a worked portion are shown. On the other hand, FIG. 14 is a measurement screen showing a working example of a slide mode, wherein a post-working plan view 60 and an average cross-sectional view 61 of a worked portion are shown.

The worked sample is an optical mask constituted of a two-layered film in which projections (defects) are formed in a line-and-space manner.

Figure 14:
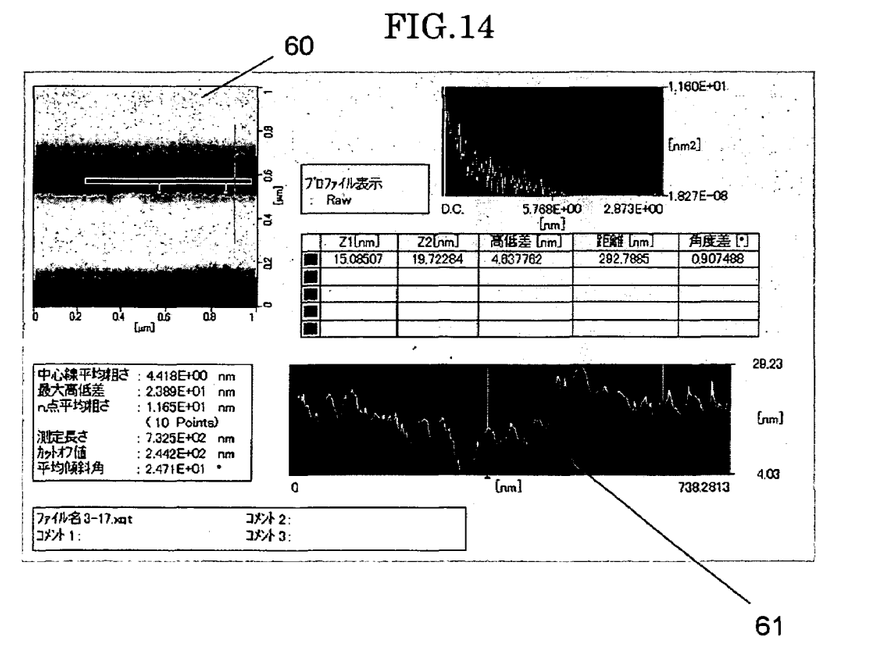
FIG. 14 is a view showing a measurement screen exemplifying an example of working in a slice mode.

As shown in FIG. 13 and FIG. 14, while a stepped portion after working in the in the contact mode is 20 nm, a stepped portion after working in the slide mode is 5 nm. This implies that the slide mode can obtain the working with more improved working flatness on the interface of the two-layered film than the contact mode.

In the slide mode of this embodiment, the probe is forcibly vibrated at low frequency using the scanner by way of the sample base side. In place of such vibrations, the probe sided may be vibrated at low frequency using the piezoelectric plate. Due to such vibrations, the probe is vibrated relative to the sample.

Further, in this embodiment, the probe is vibrated forcibly at low frequency only in the direction orthogonal to the working surface of the sample.

In place of such vibrations, the probe side may be forcibly vibrated at low frequency in the direction parallel to the working surface of the sample 2. In this case, the probe 6a may be forcibly vibrated only in one direction out of two directions consisting of the X direction and the Y direction. Further, in this case, the probe may be forcibly vibrated at low frequency in both of the direction orthogonal to the working surface of the sample 2 and the direction parallel to the working surface of the sample 2. Also, in this case, it is confirmed that this can obtain the substantially equal advantageous effects as the methods explained in conjunction with the above-mentioned embodiments.

Further, when the probe 6a is vibrated at low frequency in one direction (Z direction, X direction or Y direction) or when the probe 6a is vibrated at low frequency in both directions (Z direction and X direction, or Z direction and Y direction), in addition to the vibrations at low frequency, the surface of the sample 2 may be worked by resonating the probe 6a in the X direction or the Y direction using the XY resonance piezoelectric plate 7 shown in FIG. 1, or by resonating the probe 6a in the Z direction using the Z resonance piezoelectric plate 8 shown in FIG. 1, or by resonating the probe 6a in the X direction or the Y direction using the XY resonance piezoelectric plate 7 and, at the same time, by resonating the probe 6a in the Z direction using the Z resonance piezoelectric plate 7.

In this case, the frequency used for performing the resonance vibrations is frequency which is far higher than the frequency used for performing the vibrations by the Z scanner or the XY scanner, that is, approximately 100 KHz to 5 MHz, wherein the resonance frequency is 0.5 to 500 nm.

Further, it is also confirmed that when a metal film having toughness such as a chromium film is to be worked, by applying the high-frequency vibrations in the Z direction to the probe, cut debris which is adhered to the probe is liable to be easily peeled off thus enhancing the reproducibility of the working.

What is claimed is:

1. A working method using a scanning probe which works an object to be worked by performing relative scanning of a probe which is supported on a distal end of a cantilever on the object to be worked at a predetermined speed, wherein
the probe works the object to be worked in a state that the probe is forcibly and relatively vibrated in the direction orthogonal to a working surface of the object to be worked at low frequency of 100 to 1000 Hz.

2. A working method using a scanning probe according to claim 1, wherein the probe works the object to be worked in a state that the probe is forcibly and relatively vibrated in the direction parallel to a working surface of the object to be worked at low frequency of 100 to 1000 Hz.

3. A working method using a scanning probe according to claim 1, wherein the object to be worked is worked by setting an amplitude when the probe is forcibly and relatively vibrated at low frequency to a value which falls within a range of 5 to 2000 nm.

4. A working method using a scanning probe according to claim 1, wherein the object to be worked is worked in a state that the probe is forcibly and relatively vibrated at low frequency and, at the same time, the object to be worked is relatively resonated at frequency higher than the low frequency in the direction orthogonal to a working surface of the object to be worked.

5. A working method using a scanning probe according to claim 1, wherein the object to be worked is worked in a state that the probe is forcibly and relatively vibrated at low frequency and, at the same time, the object to be worked is relatively resonated at frequency higher than the low frequency in the direction parallel to a working surface of the object to be worked.

6. A working method using a scanning probe which works an object to be worked by performing relative scanning of a probe which is supported on a distal end of a cantilever on the object to be worked at a predetermined speed, wherein
the probe works the object to be worked in a state that the probe is forcibly and relatively vibrated in the direction parallel to a working surface of the object to be worked at low frequency of 100 to 1000 Hz.

7. A working method using a scanning probe according to claim 6, wherein the object to be worked is worked by setting an amplitude when the probe is forcibly and relatively vibrated at low frequency to a value which falls within a range of 5 to 2000 nm.

8. A working method using a scanning probe according to claim 6, wherein the object to be worked is worked in a state that the probe is forcibly and relatively vibrated at low frequency and, at the same time, the object to be worked is relatively resonated at frequency higher than the low frequency in the direction orthogonal to a working surface of the object to be worked.

9. A working method using a scanning probe according to claim 6, wherein the object to be worked is worked in a state that the probe is forcibly and relatively vibrated at low frequency and, at the same time, the object to be worked is relatively resonated at frequency higher than the low frequency in the direction parallel to a working surface of the object to be worked.

10. A working method using a scanning probe which works an object to be worked by performing relative scanning of a probe which is supported on a distal end of a cantilever on the object to be worked at a predetermined speed, wherein
the probe is fixed at a predetermined working height from a reference surface of the object to be worked, and the object to be worked is worked by scanning the probe in the X direction or in the Y direction parallel to a working surface of the object to be worked.

11. A working method using a scanning probe according to claim 10, wherein the object to be worked is worked in a state that the probe is forcibly and relatively vibrated in the direction orthogonal to the working surface of the object to be worked at low frequency of 100 to 1000 Hz.

12. A working method using a scanning probe according to claim 11, wherein the object to be worked is worked by setting an amplitude when the probe is forcibly and relatively vibrated at low frequency to a value which falls within a range of 5 to 2000 nm.

13. A working method using a scanning probe according to claim 11, wherein the object to be worked is worked in a state that the probe is forcibly and relatively vibrated at low frequency and, at the same time, the object to be worked is relatively resonated at frequency higher than the low frequency in the direction orthogonal to a working surface of the object to be worked.

14. A working method using a scanning probe according to claim 10, wherein the object to be worked is worked in a state that the probe is forcibly and relatively vibrated in the direction parallel to the working surface of the object to be worked at low frequency of 100 to 1000 Hz.

15. A working method using a scanning probe according to claim 14, wherein the object to be worked is worked by setting an amplitude when the probe is forcibly and relatively vibrated at low frequency to a value which falls within a range of 5 to 2000 nm.

16. A working method using a scanning probe according to claim 14, wherein the object to be worked is worked in a state that the probe is forcibly and relatively vibrated at low frequency and, at the same time, the object to be worked is relatively resonated at frequency higher than the low frequency in the direction orthogonal to a working surface of the object to be worked.

17. A working method using a scanning probe according to claim 10, wherein the object to be worked is worked in a state that the probe is forcibly and relatively vibrated in both directions orthogonal to and parallel to the working surface of the object to be worked at low frequency of 100 to 1000 Hz.

18. A working method using a scanning probe according to claim 17, wherein the object to be worked is worked by setting an amplitude when the probe is forcibly and relatively vibrated at low frequency to a value which falls within a range of 5 to 2000 nm.

19. A working method using a scanning probe according to claim 10, wherein the object to be worked is worked in a state that the probe is forcibly and relatively vibrated at low frequency and, at the same time, the object to be worked is relatively resonated at frequency higher than the low frequency in the direction orthogonal to a working surface of the object to be worked.

20. A working method using a scanning probe according to claim 10, wherein the object to be worked is worked in a state that the probe is forcibly and relatively vibrated at low frequency and, at the same time, the object to be worked is relatively resonated at frequency higher than the low frequency in the direction parallel to a working surface of the object to be worked.

* * * * *